United States Patent [19]

Kathawala

[11] 4,251,521

[45] Feb. 17, 1981

[54] ALKYL DIARYL SULFONIUM SALTS

[75] Inventor: Faizulla G. Kathawala, West Orange, N.J.

[73] Assignee: Sandoz, Inc., E. Hanover, N.J.

[21] Appl. No.: 10,014

[22] Filed: Feb. 7, 1979

[51] Int. Cl.³ .................... A61K 31/69; A61K 31/095
[52] U.S. Cl. .................... 424/185; 424/335;
568/18; 568/74
[58] Field of Search .............. 424/185, 335; 260/607 B

[56] References Cited

U.S. PATENT DOCUMENTS

| | | | |
|---|---|---|---|
| 2,193,963 | 3/1940 | Harris | 260/607 B |
| 2,800,747 | 7/1957 | Pitt | 260/607 B |
| 3,159,682 | 12/1964 | Baird et al. | 260/607 |
| 3,534,105 | 10/1970 | Distler et al. | 260/607 B |
| 4,034,046 | 7/1977 | Lamberti et al. | 260/607 B |

FOREIGN PATENT DOCUMENTS 2130775  12/1972  Fed. Rep. of Germany .......... 424/335

OTHER PUBLICATIONS

Freedlander et al –Proc. Soc. Exptl. Biol. Med. 63 319–322 (1946).
Chem. Abstracts vol. 66, 1967, 65309q; vol. 83, 1975, 788571.

*Primary Examiner*—Frederick E. Waddell
*Attorney, Agent, or Firm*—Gerald D. Sharkin; Richard E. Vila; Frederick H. Weinfeldt

[57] ABSTRACT

Alkyl diaryl sulfonium salts, e.g., cyclopropyl diphenylsulfonium tetrafluoroborate, are useful as hypoglycemic agents.

11 Claims, No Drawings

ALKYL DIARYL SULFONIUM SALTS

This invention relates to alkyl diarylsulfonium salts useful as hypoglycemic agents, and more particularly to pharmaceutical compositions containing such compounds, as well as to the pharmaceutical use of such compounds, and to such of said compounds which are novel.

The hypoglycemic compounds involved in this invention may be conveniently represented by the formula I:

wherein
each of R and R', is independently, a hydrogen atom, halo of atomic weight of from 18 to 80, ie. fluoro, chloro or bromo, lower alkyl, e.g., having from 1 to 4 carbon atoms,
  e.g., methyl, or lower alkoxy, e.g., having from 1 to 4 carbon atoms, e.g., methoxy;
$R^1$ is
(a) an alkyl radical having from 1 to 7 carbon atoms;
(b) a 3-haloalkyl of the formula:

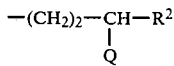

in which Q is a halogen having an atomic weight of from about 18 to 80, i.e., fluoro, chloro or bromo; or
(c) a cycloalkyl radical of the formula:

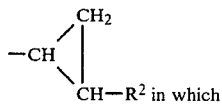

$R^2$ is a hydrogen atom, methyl or ethyl; and
$Z^\ominus$ is an anion forming a pharmaceutically acceptable, non-toxic salt of the corresponding cation.

When $R^1$ is alkyl (type a) it is further devisable into types:
  (a¹')—alkyl having 1 or 2 carbon atoms, i.e., methyl or ethyl;
  (a¹'')—alkyl having from 3 to 5 carbon atoms; e.g., n-propyl, n-butyl or -n-pentyl; and
  (a¹''')—alkyl having from 6 to 7 carbon atoms.

When $R^1$ is alkyl, it may be branched or unbranched, but is preferably unbranched. When $R^1$ is an alkyl of type a¹'' (3 to 5 carbons) and is unbranched it may be represented by the formula:

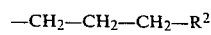

in which $R^2$ is as defined above.

It will be noted that the formula for $R^1$ when it is of type (b) and of type (a¹'') when unbranched, may be combined to be represented by the formula (e):

$$-CH_2-CH_2-\underset{\underset{Q'}{|}}{\overset{\overset{H}{|}}{C}}-R^2 \qquad (e)$$

in which
$R^2$ is as defined above; and
Q' is either hydrogen or halo having an atomic weight of from 34 to 80, i.e., chloro or bromo;

Some compounds I are known and their preparation is described in the literature; i.e., compounds I in which each of R and R' is a hydrogen atom, $Z^\ominus$ is $BF_4^\ominus$, and $R^1$ is unsubstituted- or 2-methyl-cyclopropyl, or 3-chloro- or 3-bromo-n-propyl being disclosed in J.A.C.S. 95, 5298 (1973), and compounds I in which each of R and R' is a hydrogen atom, $Z^\ominus$ is $BF_4^\ominus$, or $ClO_4^\ominus$, and $R^1$ is lower alkyl, such as ethyl, butyl or hexyl, being disclosed in Chem. Berichte 94, 2942 (1961). Also known are methyldiphenylsulfonium nitrate (Proc. Soc. Exptl. Biol. Med. 63, 319–22; 1946); ethyl, propyl and n-butyldi(p-chlorophenyl)sulfonium perchlorate (Nippon Kagaku Zasshi 87(5) 456–9; 1966); n-propyldiphenylsulfonium bromide (Werkst. Korros 22 (11), 930–3; 1971); and lower alkyl (n-propyl and n-butyl) diphenylsulfonium trifluoromethanesulfonate (J.O.C. 38(16), 2806–9; 1973). No pharmaceutical use has been disclosed for any known compound to my knowledge.

An embodiment of this invention is the use of compounds I as hypoglycemic agents as described hereinafter.

Another embodiment of this invention are those compounds I which are novel. Accordingly, novel compounds of this invention include: (a) compounds I in which $Z^\ominus$ is $Br^\ominus$, $NO_3^\ominus$ or $CF_3SO_3$ and either; (i) $R^1$ is haloalkyl (type (b), above) or cycloalkyl (type (c), above) or (ii) at least one of R and R' is other than hydrogen; (b) compounds I in which $Z^\ominus$ is $BF_4^\ominus$ and at least one of R and R' is other than hydrogen; (c) compounds I where $Z^\ominus$ is $ClO_4^\ominus$ and at least one of R and R' is either alkyl or alkoxy; (d) compounds I where $Z^\ominus$ is $ClO_4^\ominus$ and $R^1$ is either of types (b) or (c), ie. a haloalkyl or cycloalkyl radical; and (e) and all compounds I in which $Z^\ominus$ is other than $BF_4^\ominus$, $ClO_4^\ominus$, $Br^\ominus$, $NO_3^\ominus$ and $CF_3SO_3^\ominus$.

The class of compounds I may be viewed as consisting of the following subclasses Ia, Ib or Ic depending upon the nature of the $R^1$ moiety:

in which
Z is as defined above,
A is $R^1$ when it is of type (a), i.e., alkyl,
Ar is

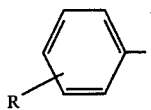

in which R is as defined above, and Ar' is

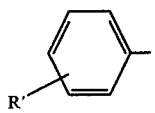

in which R' is as defined above;

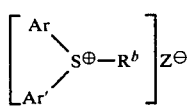
Ib in which Ar, Ar', and Z are as defined above, and $R^b$ is $R^1$ when it is of type (b), i.e., 3-haloalkyl; and

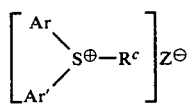
Ic in which Ar, Ar' and Z are as defined above, and $R^c$ is $R^1$ when it is of type (c).

As noted above, some compounds I are known and their preparation is described in the literature. Those compounds I which are not known may be prepared in a manner analogous to the methods described in the literature for the preparation of the known compounds, or in accordance with the disclosure herein.

Depending upon the type of compound I, ie. Ia, Ib or Ic, and the type of salt form desired, one or more of several preparative procedures may be employed.

For example, a convenient method of preparing compounds Ic is by cyclizing (process a) a compound Ib°; ie. a Compound Ib in which Q is chloro or bromo. The cyclization may be accomplished by treating a Compound Ib° in a suitable inert organic solvent, e.g. a cyclic ether such as tetrahydrofuran with a strong base, e.g. a hydride such as sodium hydride, sodamide, or potassium tertiary butoxide, at moderate temperatures, e.g. 15° to 35° C., preferably at room temperature under essentially anhydrous conditions.

For purposes of illustrating certain other preparative procedures and various embodiments, the compounds I may be further divided into subclasses Ia', Ib' and Ic', as follows:

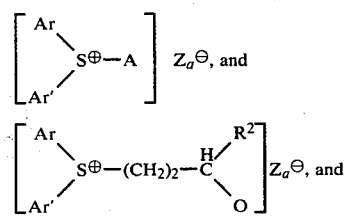

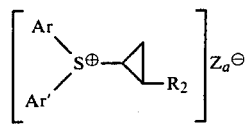
Ic' wherein Ar, Ar', $R^2$, Q and A are as defined above, and $Z_a^\ominus$ represents the anion of solvent soluble $MZ_a$ salt in which M is a cation which is capable of forming with a halogen anion a salt that is either per se insoluble or relatively less soluble than the $MZ_a$ salt in the solvent.

As an illustration, Compounds Ia' or Ib', may conveniently be prepared by reacting (process b) a suitable diarylsulfide of formula II:

in which Ar and Ar' are as defined above, with an appropriate alkyliodide or haloalkyliodide of the formula IIIa or IIIb:

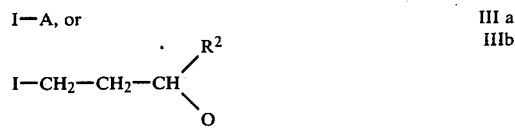

in which A, $R^2$ and Q are as defined above, respectfully, in the presence of at least one equivalent of the salt $MZ_a$ under essentially anhydrous conditions, at moderate temperatures, e.g., from 15° to 40° C., e.g., at room temperature, in an inert organic solvent, preferably a polar solvent, e.g., nitromethane. The reactants II and IIIa (or IIIb) are conveniently mixed in the solvent, in a suitable vessel and exercising such caution as may be necessary such as shielding from light, the salt $MZ_a$ may be added in a single portion. The reaction is preferably carried out under an inert atmosphere, e.g., dry nitrogen. An excess of a compound IIIa (or IIIb) is preferably employed. Illustrative of various $MZ_a$ salts include the salts of noble metals of which silver represents a preferred metal. Representative anions forming such salts include the tetrafluoroborate, perchlorate and trifluoromethylsulfonate ions. Examples of preferred salts include silver tetrafluoroborate and silver trifluoromethylsulfonate of which silver tetrafluoroborate is especially preferred. The resulting solvent insoluble salt, MI, is separated by known techniques and the desired product recovered from the solvent phase by applying conventional procedures to be selected in large part on the nature of the compound I being produced and the complexity of the remaining solvent reaction medium.

Process (b) may also be carried out employing bromide analogues of the iodides of compounds IIIa and IIIb, in which case the solvent insoluble salt will be of the formula MBr, provided of course that any halogen represented by Q is other than bromo, ie it is F or Cl.

In other preparative procedures that may be defined as ion exchange reactions (generally herein designated process C), the compounds of the formula I may be converted into other salt forms.

For example, in a procedure herein designated process C-1, a compound of the formula I":

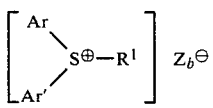  (I″)

may be converted into a compound of the formula I‴:

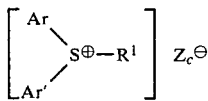  (I‴)

with Ar, Ar′ and $R^I$ in formulae I″ and I‴ being as above defined, and wherein $Z_c^\ominus$ is an anion forming a less water soluble compound I than formed with the anion $Z_b^\ominus$. Conversely, the anion $Z_b^\ominus$ is anion forming a more water soluble compound I than is formed with the anion $Z_c^\ominus$.

More particularly, the compounds of the formula I‴ may be prepared in process C-1 by heating a compound I″ in aqueous solution in the presence of an acid of the formula IV:

$$H\text{—}Z_c \quad\quad (IV)$$

wherein $Z_c$ is as above defined, at temperatures typically of from about 65° C. to 120° C., desirably in the presence of a theoretical excess of the acid of the formula IV.

Preferred compounds of the formula I″ include those in which $Z_b^\ominus$ is the tetrafluoroborate ion. By way of illustration, compounds of the formula I‴ in which $Z_c^\ominus$ is the perchlorate ion ($ClO_4^\ominus$) are preferably prepared from compound I″ in which $Z_b^\ominus$ is $BF_4^\ominus$, preferably by heating such a compound I″ in the presence of an excess of perchloric acid in an aqueous solution at temperatures of from 70° C. to 85° C. Similarly, the compounds of the formula I‴ in which $Z_c^\ominus$ is the methylsulfonate ion, the benzenesulfonate ion or the p-toluenesulfonate ion are preferably prepared by heating a compound I″ in which $Z_b^\ominus$ is the tetrafluoroborate ion in an aqueous solution at temperatures of from 85° C. to 100° C. in the presence of an excess of the acid corresponding to the desired anion, ie. methylsulfonic acid, benzenesulfonic acid or p-toluenesulfonic acid.

The desired compound I‴ in process C-1 may be initially isolated by taking advantage of its reduced water solubility, eg. by lowering the temperature of the resulting reaction mixture.

Another ion exchange procedure that is particularly convenient (and is herein designated process C-2) involves generally the reaction of a compound $I^{iv}$.

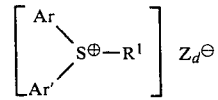  ($I^{iv}$)

with a compound of the V:

$$M_aZ_c \quad\quad V$$

in an aqueous solution to obtain a compound of the formula $I^v$:

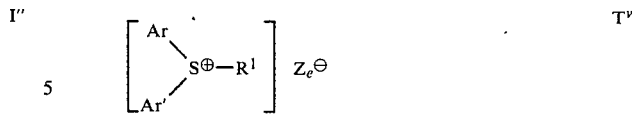

with Ar, Ar′ and $R^1$ in formulae $I^{iv}$ and $I^v$ being as above defined, and wherein $M_a$ is a metal cation forming with the anion $Z_d^\ominus$ a salt $M_aZ_d$ that is less water soluble than the compound $I^v$, $Z_e$ is an anion forming with $M_a$ the water soluble salt V that is more water soluble than $M_aZ_d$ and $Z_d^\ominus$ is conversely an anion forming with $M_a$ the salt $M_aZ_d$.

The process C-2 is more particularly carried out in an aqueous solution at temperatures preferably in the range of 50° C. to 120° C., more preferably 80° C. to 100° C., preferably with a theoretical excess of the compound V.

By way of illustration, a preferred embodiment of process C-2 involves the use of a compound $I^{iv}$ in which $Z_d^\ominus$ is the tetrafluoroborate anion and $M_a$ is potassium whereby the highly water insoluble potassium tetrafluoroborate is formed as a result of the reaction and separated from the reaction mixture by taking advantage of its water insolubility. In such embodiment representative and preferred compounds of the formula V include those in which $Z_e$ is the bromide ion (potassium bromide), the p-toluene-sulfonate ion (potassium p-toluenesulfonate), the bisulfate ion (potassium bisulfate) and the naphthalene-2-sulfonate ion (potassium naphthalene-2-sulfonate).

Processes C-1 and C-2, particularly process C-1, may be manipulated in various ways to improve desired results. For example, the compounds I″ or $I^{iv}$ that are difficult to dissolve in water may be used in conjunction with an alkali metal hydroxide such as potassium hydroxide or sodium hydroxide, particularly potassium hydroxide, to improve the solubility of such starting material.

Other known ion exchange procedures such as those involving ion exchange resins may be employed, especially when representing a convenient method of separating desired products from reactants and starting materials in those procedures specifically detailed above, eg. processes C-1 and C-2. Typical ion exchange resins for such use are well known and are represented, for example, by the product obtainable under the trademark Dowex 1-X8. Final recovery and refinement of the desired product of the formula I may also be effected by other conventional techniques, eg. by crystallization, precipitation, distillation or chromatographic procedures, including thin layer and column chromatography. Typical chromatography additives for such use are well known and are represented, for example, by the products obtainable under the trademarks Amberlite XAD-2 and Sephadex LH2O.

Various other ways of employing ion exchange procedures, such as those specifically detailed above, will be recognized by those skilled in the art. For example, procedures such as processes C-1 and C-2, above, may be combined with processes (a) and (b), above, as the final stages thereof, in order to obtain the ultimately desired compound I from an intermediary compound I without effecting an actual recovery of the latter.

Starting materials and reagents used in the abovedescribed reactions, e.g., compounds II, IIIa, IIIb, IV and V are either known and obtained by methods described in the literature, or where not known, may be obtained by methods analogous to those described in the literature.

UTILITY

The compounds of formula I are useful because they possess pharmacological activities in animals. In particular Compounds I are useful as hypoglycemic agents, i.e. in the lowering of blood serum sugar levels, e.g. in the treatment of diabetes, as evidenced, for example, in a hypoglycemic test on fasted laboratory mice. In said test a population of male mice of the ICR strain, weighing from about 30 to 35 grams (6 to 8 weeks old) are fasted 16 hours, one group are dosed orally with test compound (10 to 200 mg/kg dose) and a control group receiving 0.5% carboxymethyl cellulose (CMC) is run concurrently. Two hours later, mice are anethetized with sodium hexabarbital (85 mg/kg i.p.), whereupon blood is collected by cardiac puncture. The blood is placed in AutoAnalyzer Cup containing 0.025 cc of heparin (1000 units/ml). Blood samples are capped, shaken and kept in ice bucket. Glucose is determined by the AutoAnalyzer potassium ferric-cyanide method #N-2b of Technicon Corp. To validate the experiment a known hypoglycemic standard is included.

In addition to their general usage as hypoglycemic agents, Compounds I are particularly useful in the treatment of juvenile diabetes, as evidenced, for example in hypoglycemic tests carried out on diabetic mice, e.g. mice showing a positive urine Clinistix ®* reaction 6 days after being injected (in the tail vein) with fresh streptozotocin (175 mg/kg in citrate buffer, pH 4.5).

*Clinistix ® reagent strips are obtainable commercially from Ames Co. (Div. of Miles Laboratories, Inc. Elkhart, Ind.); having the ingredients in the reagent: 4% w/w glucose oxidase (0.4 I.U.); 0.4% w/w peroxidase (900 I.U.; 3.8% w/w orthotolidine; 65% w/w buffer; 27.8% w/w non-reactive ingredients.

For the above-described usage, compounds of formula I may be combined with one or more pharmaceutically acceptable carriers, e.g. solvents, diluents and the like, and administered orally in such forms as tablets, capsules, dispersible powders, granules, suspensions containing, for example, from about 0.5 to 5% of suspending agent, syrups containing, for example, from about 10 to 50% of sugar, and elixirs containing, for example from about 20 to 50% of ethanol, and the like. These pharmaceutical preparations may contain, for example, from about 0.5% up to about 90% of the active ingredient based on the total weight of mixture, i.e., in combination with the carrier, and adjuvants included as desired, more usually between 5% and 70% by weight of such mixture.

Effective dosages will vary depending upon such factors as the particular compound employed and the severity of the condition being treated. However, satisfactory results are generally obtained when the compounds are administered at a daily dosage of from about one milligram to about 50 milligrams per kilogram of animal body weight orally. Administration daily may be as a single daily dose, or in multiple divided doses, e.g. from 2 to 4 doses, to obtain the desired level of administration. For most large mammals, the total daily dosage is from about 50 milligrams to about 3000 milligrams. Dosage forms suitable for internal administration comprise from about 10 to about 1500 milligrams of the active compound, e.g. in intimate admixture with one or more pharmaceutically acceptable carriers. Liquid carriers include sterile water, polyethylene glycols and edible oils such as corn, peanut and sesame oils. Solid carriers include lactose, calcium carbonate, calcium phosphate and kaolin. Tablets and solid-or liquid-filled capsules, are the preferred forms. Solid forms are preferred.

A representative formulation suitable for oral administration is a tablet or capsule prepared by standard tableting or encapsulating techniques which contains the following and may be administered 2 to 4 times a day to reduce the blood serum glucose level of a mammal suffering from juvenile diabetes:

| Ingredient | Weight (mg.) | |
|---|---|---|
| | tablet | capsule |
| cyclopropyldiphenyl sulfonium tetrafluoroborate | 100 | 100 |
| tragacanth | 10 | — |
| lactose | 247.5 | 300 |
| corn starch | 25 | |
| talcum | 15 | |
| magnesium stearate | 2.5 | |
| TOTAL | 400 mg. | 400 mg. |

Salts (the values of $Z^\ominus$) judged to be of particular interest generally include the tetrafluoroborate, perchlorate, bisulfate, methanesulfonate, phenylsulfonate, p-toluenesulfonate, bromide, trifluoromethylsulfonate, the naphthalenesulfonates, eg. the naphthalene-2-sulfonate, acetate, benzoate and maleate.

Preferred compounds I of the present invention are characterized by one or both of the following features:

(a) compounds in which R and R' are the same and at the same relative position as may be represented by the partial formula:

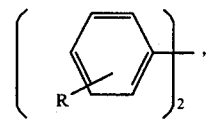

including compounds in which R is hydrogen as well as halo, alkyl or alkoxy; and (b) compound I in which $R^1$ is of the type (c) as given above.

The more preferred compounds I are characterized by one or both of the following features: (a) those in which R and R' are both hydrogen; and (b) those in which $R^1$ is cyclopropyl. Representative preferred compounds I include tetrafluoroborate, perchlorate, p-toluenesulfonate, maleate and bromide cyclopropyldiphenylsulfonium salts.

In the following examples, which illustrate the invention, temperatures are in degrees centigrade, and room temperature is 20° to 30° C., unless indicated otherwise.

EXAMPLE 1

3-Chloropropyldiphenylsulfonium Tetrafluoroborate

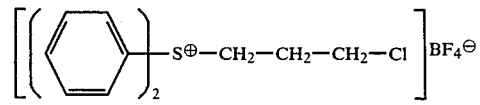

A solution of diphenyl sulfide (93.0 g, 0.5 mol), 1-chloro-3-iodopropane (347 g, 1.70 mol), and 200 ml of nitromethane is stirred in a vessel at room temperature under nitrogen. The vessel is shielded from light. Silver tetrafluoroborate (78.0 g, 0.40 mol) is added in one portion. Initially the temperature rises to about 40°, then gradually falls to room temperature. No external cooling is applied. After 16 hr, 200 ml of methylene chloride is added and the mixture is filtered through a sintered glass funnel prepared with a pad of 35 g of Fluorisil to facilitate removal of the suspended silver salts. The solids are washed with methylene chloride and the methylene chloride portions combined. The combined methylene chloride solution (containing the product and residual starting material) is evaporated until a solid appears, then 1 liter of ether is added gradually to precipitate the sulfonium salt as an oil. Upon vigorous shaking of the mixture to extract out of the oily sulfonium salt layer, the excess starting material induces crystallization. The crystals of 3-Chloropropyldiphenylsulfonium tetrafluoroborate are collected, washed with ether, and dried in vacuo at 25°, mp 104–105.

Repeating the procedure of this example but using in place of the 1-chloro-3-iodopropane, an equivalent amount of:
(a) n-iodopropane
(b) n-iodopentane;
(c) 3-chloro-1-iodobutane;
(d) methyl iodide; or
(e) n-iodohexane;
there is accordingly obtained, respectively,
(a) n-propyl diphenylsulfonium tetrafluoroborate; m.p. 112°–114° C.
(b) n-pentyl diphenylsulfonium tetrafluoroborate; as an oil;
(c) 3-chlorobutyl diphenylsulfonium tetrafluoroborate;
(d) methyl diphenylsulfonium tetrafluoroborate; as an oil;
(e) n-hexyl diphenylsulfonium tetrafluoroborate; m.p. 51°–54° C.

Repeating the procedure of this example but using in place of the diphenylsulfide, an equivalent amount of:
(f) di(p-tolyl) sulfide;
(g) di(p-methoxyphenyl)sulfide;
(h) phenyl p-tolyl sulfide; or
(i) p-methoxyphenyl phenylsulfide;
there is accordingly obtained, respectively,
(j) 3-chloropropyldi(p-tolyl)sulfonium tetrafluoroborate; m.p. 145°–147° C.
(k) 3-chloropropyldi(p-methoxyphenyl)sulfonium tetrafluoroborate; m.p. 72°–73° C.
(l) 3-chloropropylphenyl p-tolylsulfonium tetrafluoroborate; and
(m) 3-chloropropyl p-methoxyphenyl phenylsulfonium tetrafluoroborate.

Repeating the above-described procedures and employing appropriate starting materials in appropriate amounts there is similarly obtained:
(n) n-propyldi(p-tolyl)sulfonium tetrafluoroborate;
(o) n-propyl phenyl p-tolylsulfonium tetrafluoroborate.

EXAMPLE 2

Cyclopropyldiphenylsulfonium tetrafluoroborate

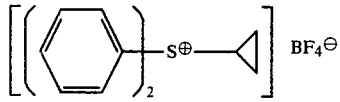

A suspension of 3-chloropropyldiphenylsulfonium tetrafluoroborate (118.7 g, 0.339 mol) in dry tetrahydrofuran (500 ml) is placed in a 2 liter flask under nitrogen. Then 5 g. portions of a 55% sodium hydridemineral oil dispersion (15.2 g, 0.350 mol), are added in 0.5-hr. intervals. The resulting mixture is stirred at room temperature for 24 hr. A solution of 25 ml of 48% tetrafluoroboric acid, 15 g of sodium tetrafluoroborate, and 400 ml of water are added to destroy residual hydride and swamp out chloride ion. After 5 min., methylene chloride (300 ml) is added, and the methylene chloride layer is removed from the lower aqueous layer. As the densities of the methylene chloride and water layers are nearly equal, caution is required in recovering the desired methylene chloride layer; the aqueous layer is retained for further extraction. The methylene chloride solution is then washed with 100 ml of water; the aqueous layer is separated and combined with the first aqueous layer. The combined water layers are extracted with an additional 100 ml of methylene chloride. The methylene chloride portions are combined, dried over anhydrous sodium sulfate, and evaporated in vacuo until precipitation occurs. The title product is precipitated upon addition of ether (1 liter). The solid product is collected, washed with ether, and recrystallized from absolute ethanol (approximately 400 ml) and dried in vacuo, mp 139°.

Repeating the procedure of this example, but using in place of the 3-chloropropyldiphenylsulfonium tetrafluoroborate, an equivalent amount of:
(a) 3-chlorobutyldiphenylsulfonium tetrafluoroborate; or
(b) 3-chloropropyldi(p-tolyl)sulfonium tetrafluoroborate;
there is accordingly obtained, respectively:
(a) 2-methylcyclopropyldiphenylsulfonium tetrafluoroborate; and
(b) cyclopropyldi(p-tolyl)sulfonium tetrafluoroborate; m.p. 110°–113° C.

EXAMPLE 3

Cyclopropyldiphenylsulfonium perchlorate 5.0 g cyclopropyldiphenylsulfonium tetrafluoroborate is dissolved in 50 ml distilled water by heating on a steam bath. To the resulting solution is then added 15 ml of 48% perchloric acid. The solution is then cooled and the precipitate which results filtered, washed with water, and dried under vacuum to give cyclopropyldiphenylsulfonium perchlorate m.p. 144°–146°.

Repeating the general procedure of this example using appropriate starting materials there is likewise prepared
(a) propyldiphenylsulfonium perchlorate; and
(b) 3-chloropropyldiphenylsulfonium perchlorate.

EXAMPLE 4

Cyclopropyldiphenylsulfonium p-Toluenesulfonate

To a solution of 12.0 g cyclopropyldiphenylsulfonium tetrafluoroborate in 200 ml distilled water and 25 ml 2 N aqueous sodium hydroxide at 100°, is added gradually a solution of 60.0 g para-toluenesulfonic acid in 200 ml distilled water. The resulting mixture is cooled and extracted several times with methylene chloride. The combined methylene chloride extracts, after washing with water, are dried over anhydrous sodium sulfate filtered and evaporated in vacuo to dryness to obtain a residue. From the residue is crystallized from ethanol, the unreacted cyclopropyl diphenyl sulfonium tetrafluoroborate which is separated by filtering, and the mother liquor evaporated to dryness to obtain a residue.

The residue thereby obtained in treated again as above with lesser amounts of ethanol until all the unreacted starting material is removed, to leave behind refined cyclopropyldiphenylsulfonium p-toluene sulfonate as a viscous oil, which may then be crystallized from methylene chloride-ether (20:1); m.p. 84°–87°.

Repeating the procedure of this example, but using in place of the p-toluenesulfonic acid, an equivalent amount of p-methylsulfonic acid or benzene sulfonic acid there is accordingly obtained cyclopropyldiphenylsulfonium p-methylsulfonate; and cyclopropyl diphenylsulfonium p-phenylsulfonate, respectively.

EXAMPLE 5

Following the procedures of Examples 1 and 4 and employing the appropriate starting materials, there is accordingly obtained:

(a) n-propyldiphenylsulfonium p-toluenesulfonate;
(b) 3-chloropropyldiphenylsulfonium p-toluenesulfonate;
(c) n-propyl p-tolyl phenylsulfonium p-toluenesulfonate.

EXAMPLE 6

Cyclopropyldiphenylsulfonium bromide

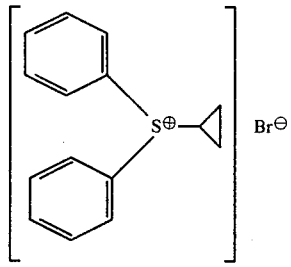

5.0 g of cyclopropyl diphenyl sulfonium tetrafluoroborate is dissolved in 30 ml. water by heating to 90°–95° C. To this hot solution is then added 50 ml. of a solution of 53 g. potassium bromide in 100 ml. water. The reaction mixture is stirred well and allowed to cool to room temperature. The white precipitate of potassium tetrafluoroborate thus formed is filtered off; and the aqueous filtrate is extracted several times with methylene chloride. The combined organic phase is then dried over sodium sulfate, filtered and evaporated to dryness i.v. The residue is triturated with ether to obtain cyclopropyldiphenylsulfonium bromide, m.p. 160°–161° C.

EXAMPLE 6A

Following the procedure of Example 6, the following compounds are prepared:

(a) cyclopropyldiphenylsulfonium p-toluenesulfonate, m.p. 84°–85° C.
(b) cyclopropyldiphenylsulfonium bisulfate (HSO4⊖), m.p. 114°–115° C.

EXAMPLE 7

Diphenyl-α-chloropropylsulfonium trifluoromethyl sulphonate

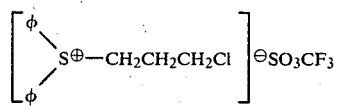

To a solution of 2.8 g. diphenyl sulphide and 5.1 g. 1-chloro-3-iodopropane in 50 ml. nitromethane is added 2.6 g. silver trifluoro methane sulphonate. The reaction mixture is stirred at room temperature with exclusion of moisture and light for 48 hours. The solution mixture is then filtered free of any precipitated silver salt and the filtrate is evaporated i.v. to dryness. The residue is triturated with ether to obtain the title compound, m.p. 109–112.

EXAMPLE 8

Cyclopropyldiphenylsulfonium-2-naphthalene sulfonate

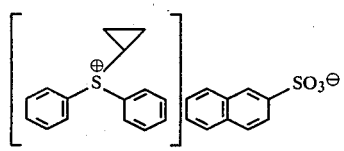

5.0 g. of cyclopropyl diphenyl sulfonium tetrafluoroborate is dissolved in 30 ml. water by heating the solution to 90°–95° C. To this is added 50 ml. of a hot solution of potassium naphthalene-2-sulfonate (obtained by heating 49.7 g. of naphthalene-2-sulfonic acid and 12 g. potassium hydroxide in 100 ml. water). The above reaction mixture is then mixed vigorously and maintained at 90° C. for a few minutes and then allowed to cool gradually to room temperature. The reaction mixture is then filtered free of any precipitate and the aqueous filtrate extracted several times with methylene chloride. The combined methylene chloride extracts, after drying over sodium sulphate, is filtered and evaporated i.v. to dryness. The residue is triturated with ether to obtain the title compound, m.p. 93°–95° C.

EXAMPLE 9

Cyclopropyldiphenylsulfonium acetate

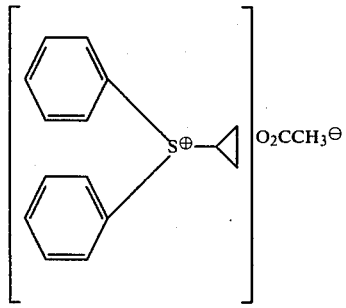

To a solution of 5.0 g. cyclopropyldiphenylsulfonium tetrafluoroborate in 30 ml. water at 90°–95° C. is added 50 ml. of hot solution of potassium acetate (obtained by mixing 26.6 g. acetic acid with 24.0 g. potassium hydroxide). The reaction mixture is stirred well and maintained at 90°-95° C. for several minutes and allowed to cool to room temperature gradually. The reaction mixture is then filtered free of any solids; the aqueous filtrate extracted several times with methylene chloride, the combined methylene chloride extracts are dried over sodium sulphate, filtered and evaporated i.v. to dryness. From the residue is obtained on trituration with ether the title product, as an oil.

EXAMPLE 10

Following the procedure of Example 9 the following additional compounds of the invention are prepared:
(a) cyclopropyldiphenylsulfonium benzoate, as an oil.
(b) cyclopropyldiphenylsulfonium maleate, as an oil.

What is claimed is:

1. A method of reducing the level of glucose in the blood of a mammal in need of such treatment comprising orally administering to such mammal a blood glucose reducing effective amount of a compound of the formula:

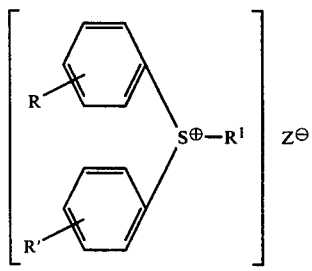

wherein each of R and R', independently, is hydrogen, fluoro, chloro, bromo, alkyl having from 1 to 4 carbon atoms, or alkoxy having from 1 to 4 carbon atoms;

$R^1$ is:

(a) alkyl having from 1 to 7 carbon atoms:

wherein $R^2$ is a hydrogen atom, methyl or ethyl; and Q is fluoro chloro or bromo; and $Z^\ominus$ is an anion forming a pharmaceutically acceptable non-toxic salt of the corresponding cation.

2. The method of claim 1 in which $R^1$ is of the type (a).

3. The method of claim 1 in which $R^1$ is of the type (b).

4. The method of claim 1 in which $R^1$ is of the type (c).

5. The method of claim 4 in which $R^2$ is hydrogen.

6. The method of claim 1 in which R and R' are each hydrogen.

7. The method of claim 6 in which the compound is cyclopropyldiphenylsulfonium tetrafluoroborate.

8. The method of claim 6 in which the compound is cyclopropyldiphenylsulfonium p-toluenesulfonate.

9. The method of claim 1 in which the compound is administered in an amount of from about 50 to about 3000 milligrams daily.

10. The method of claim 1 in which juvenile diabetes is treated.

11. A method of claim 6 in which the compound is selected from the group consisting of tetrafluoroborate, perchlorate, p-toluenesulfonate, maleate and bromide cyclopropyldiphenylsulfonium salts.

* * * * *